US011399562B2

(12) United States Patent
Stahl et al.

(10) Patent No.: US 11,399,562 B2
(45) Date of Patent: Aug. 2, 2022

(54) ORAL POUCHED PRODUCT

(71) Applicant: NCP NextGen A/S, Vejle (DK)

(72) Inventors: My Ly Lao Stahl, Vejle Ost (DK); Heidi Ziegler Bruun, Vejle Ost (DK); Bruno Provstgaard Nielsen, Vejle Ost (DK); Jesper Neergaard, Aabenraa (DK); Bine Hare Jakobsen, Ry (DK)

(73) Assignee: NCP NextGen A/S, Vejle (DK)

( * ) Notice: Subject to any disclaimer, the term of this patent is extended or adjusted under 35 U.S.C. 154(b) by 42 days.

(21) Appl. No.: 17/048,058

(22) PCT Filed: Jun. 5, 2020

(86) PCT No.: PCT/DK2020/050161
§ 371 (c)(1),
(2) Date: Oct. 15, 2020

(87) PCT Pub. No.: WO2020/244723
PCT Pub. Date: Dec. 10, 2020

(65) Prior Publication Data
US 2022/0087929 A1    Mar. 24, 2022

(30) Foreign Application Priority Data

Jun. 7, 2019  (DK) .............................. PA201900698
Sep. 30, 2019  (DK) .............................. PA201970610
Sep. 30, 2019  (DK) .............................. PA201970611
Sep. 30, 2019  (DK) .............................. PA201970612

(51) Int. Cl.
| A61K 9/00 | (2006.01) |
| A24B 15/16 | (2020.01) |
| A24B 15/30 | (2006.01) |
| A24B 15/32 | (2006.01) |
| A24B 15/38 | (2006.01) |
| A24B 15/40 | (2006.01) |
| A24B 15/42 | (2006.01) |
| A61K 31/465 | (2006.01) |
| A24B 13/00 | (2006.01) |

(52) U.S. Cl.
CPC .............. *A24B 15/16* (2013.01); *A24B 13/00* (2013.01); *A24B 15/302* (2013.01); *A24B 15/32* (2013.01); *A24B 15/385* (2013.01); *A24B 15/403* (2013.01); *A24B 15/42* (2013.01); *A61K 9/006* (2013.01); *A61K 9/009* (2013.01); *A61K 31/465* (2013.01)

(58) Field of Classification Search
None
See application file for complete search history.

(56) References Cited

U.S. PATENT DOCUMENTS

| 5,167,244 | A | 12/1992 | Kjerstad |
| 8,863,755 | B2 | 10/2014 | Zhuang et al. |
| 9,402,809 | B2 | 8/2016 | Axelsson et al. |
| 11,096,412 | B2 | 8/2021 | Stahl et al. |
| 2005/0034738 | A1 | 2/2005 | Whalen |
| 2005/0053665 | A1 | 3/2005 | Ek et al. |
| 2008/0302682 | A1 | 12/2008 | Engstrom et al. |
| 2011/0214681 | A1 | 9/2011 | Axelsson et al. |
| 2012/0247492 | A1 | 10/2012 | Kobal et al. |
| 2013/0108558 | A1 | 5/2013 | Andersen |
| 2013/0152953 | A1 | 6/2013 | Mua et al. |
| 2015/0020818 | A1 | 1/2015 | Gao et al. |
| 2015/0068545 | A1 | 3/2015 | Moldoveanu et al. |
| 2015/0096576 | A1 | 4/2015 | Gao et al. |
| 2016/0000140 | A1* | 1/2016 | Sebastian .................. B65B 9/20 131/352 |
| 2016/0165953 | A1 | 6/2016 | Goode, Jr. |
| 2016/0192703 | A1 | 7/2016 | Sebastian et al. |
| 2017/0318858 | A1* | 11/2017 | Hodin ..................... A24F 23/02 |
| 2018/0271139 | A1 | 9/2018 | Aspgren et al. |
| 2019/0037909 | A1 | 2/2019 | Greenbaum et al. |
| 2020/0297024 | A1 | 9/2020 | Bodin |

FOREIGN PATENT DOCUMENTS

| CN | 107319629 A | 11/2017 |
| EP | 2692254 A1 | 2/2014 |
| EP | 3087852 A1 | 11/2016 |
| EP | 3491940 A1 | 6/2019 |
| GB | 673587 A | 6/1952 |
| WO | 2007084587 A2 | 7/2007 |
| WO | 2007104573 A2 | 9/2007 |
| WO | 2008056135 A2 | 5/2008 |
| WO | 2009010881 A2 | 1/2009 |
| WO | 2010121619 A1 | 10/2010 |
| WO | 2012134380 A1 | 10/2012 |

(Continued)

OTHER PUBLICATIONS

Additional Search Report from Danish Patent and Trademark Office for Application No. PA 2019 70610 dated Jul. 30, 2020 (2 pages).
Additional Search Report from Danish Patent and Trademark Office for Application No. PA 2019 70612 dated Aug. 4, 2020 (2 pages).
Search Report from Danish Patent and Trademark Office for Application No. PA 2019 00698 dated Dec. 3, 2019 (1 page).
Search Report from Danish Patent and Trademark Office for Application No. PA 2019 70610 dated Feb. 5, 2020 (2 pages).
Search Report from Danish Patent and Trademark Office for Application No. Pa 2019 70611 dated Jan. 24, 2020 (2 pages).
Search Report from Danish Patent and Trademark Office for Application No. PA2019 70612 dated Feb. 3, 2020 (2 pages).

(Continued)

*Primary Examiner* — Dennis R Cordray
(74) *Attorney, Agent, or Firm* — St. Onge Steward Johnston & Reens LLC

(57) ABSTRACT

An oral pouched product is disclosed, the oral pouched product includes a saliva permeable pouch, a pouch composition, the pouch composition includes heat-treated fibers, nicotine, water in an amount of less than 65% by weight of the pouch composition, and at least one sugar alcohol. Also, a method for manufacturing an oral pouched product is disclosed.

24 Claims, No Drawings

(56) References Cited

FOREIGN PATENT DOCUMENTS

| WO | 2013090366 | A2 | 6/2013 |
|----|------------|----|--------|
| WO | 2013152918 | A1 | 10/2013 |
| WO | 2015052282 | A1 | 4/2015 |
| WO | 2015067372 | A1 | 5/2015 |
| WO | 2015193379 | A1 | 12/2015 |
| WO | 2016083463 | A1 | 6/2016 |
| WO | 2017153718 | A1 | 9/2017 |
| WO | 2018011470 | A1 | 1/2018 |
| WO | 2018126262 | A2 | 7/2018 |
| WO | 20170683 | A1 | 10/2018 |
| WO | 2018197454 | A1 | 11/2018 |
| WO | 2018233795 | A1 | 12/2018 |
| WO | 2019115778 | A1 | 6/2019 |
| WO | 2020157280 | A1 | 8/2020 |

OTHER PUBLICATIONS

International Search Report Application No. PCT/DK2020/050159; dated Aug. 12, 2020; 3 pages.
International Search Report Application No. PCT/DK2020/050160; dated Oct. 1, 2020; 3 pages.
International Search Report Application No. PCT/DK2020/050162; dated Oct. 2, 2020; 4 pages.
International Search Report Application No. PCT/DK2020/050163; dated Oct. 7, 2020; 4 pages.
Seidenberg, Andrew B., Olalekan A. Ayo-Yusuf, and Vaughan W. Rees. "Characteristics of American Snus" and Swedish Snus Products for Sale in Massachusetts, USA. Nicotine and Tobacco Research 20.2 (2018): 262-266.
Wikipedia, "Sugar alcohol"; https://en.wikipedia.org/wiki/Sugar_alcohol; downloaded from Internet on Sep. 27, 2017.

* cited by examiner

ORAL POUCHED PRODUCT

FIELD OF THE INVENTION

The invention relates to an oral pouched product and a method for manufacturing an oral pouched product.

BACKGROUND OF THE INVENTION

Delivery of nicotine by smoking has many well-known drawbacks, particular health related problem, such as inclusion of carcinogenic substances.

However, tobacco substitutes also suffer from disadvantages, such as inadequate relief of cravings for the user.

It is an object of the present invention to provide a nicotine containing pouch, e.g. as a tobacco substitute, which may solve the above problems while minimizing undesired side effects.

SUMMARY OF THE INVENTION

The invention relates to an oral pouched product comprising
   a saliva permeable pouch,
   a pouch composition,
   the pouch composition comprising
   heat-treated fibers,
   nicotine,
   water in an amount of less than 65% by weight of the pouch composition, and
   at least one sugar alcohol.

An advantage of the invention may be that an oral pouch product may be obtained having a long-life taste and mouthfeel. On one hand, a very desirable taste and mouthfeel is obtained by a combination of water, sugar alcohols and fibers providing an attractive soft, moist and moldable texture of the pouch composition.

On the other hand, this combination may be somewhat susceptible to undesirable microbial growth. Nevertheless, by utilizing nicotine also as an antimicrobial preservative, a long-life taste and mouthfeel is obtained.

An advantage of the present invention may be that an oral pouched product with a long shelf life. This may even be obtained with only low amounts of preservatives or even without preservatives. Instead, the present invention benefits from using pretreated fibers instead of e.g. tobacco, to avoid any risks associated therewith, in combination with a separate nicotine source. Thereby, the fibers may be separately pretreated before adding the volatile nicotine. Further, the nicotine is also utilized partly due to its antimicrobial characteristics and possibly even to raise the pH levels.

A further advantage of the invention may be that a desirable taste and mouthfeel may be obtained. By combining the sugar alcohol and its desirable taste and mouthfeel with an microbially resilient pouch composition, a long-term stable taste and mouthfeel is obtained. Conventional pouches typically are not focused on long-term antimicrobial stability of the products or does so by included preservatives. When shelf life has not been considered, the high water content makes the product vulnerable to microbial growth, such as growth of yeast, mold, and bacteria. This may not only compromise health safety but also leads to significant deterioration of the user experience, by visually alteration of the product, altering and deterioration of the taste etc.

A further advantage of the invention may be that a long shelf life of the product is obtained. This is obtained even if using fibers, which typically may have a relatively high content of microbes. However, by utilizing nicotine as an antibacterial agent, and possibly also as an alkaline pH regulating agent, a long shelf life is nevertheless obtained.

A further advantage of the invention is that it is not based on tobacco, and thus avoids many of the disadvantageous substances associated therewith. Further, this allows handing the texture providing fibers and the nicotine separately. Thereby, the fibers can be processed without risk of the volatile nicotine evaporating or degrading.

Using nicotine as an antimicrobial preservative has the advantage that when adjusting the amount of nicotine, the effects on the shelf-life can be taken into consideration. Thus, the ratio between nicotine and the fibers may be adjusted. This is not possible for tobacco-based products, as the fibers and the nicotine are provided by the tobacco.

Still, a further advantage of the invention may be that the improved shelf life of the product and its taste is obtained without lowering the water activity to an undesirable level where texture and mouthfeel might be compromised. Nevertheless, the present inventors surprisingly found that the improved shelf life of the product and its taste could still be obtained, even for the relatively high water activity in product.

In embodiments of the invention, this may be done without using too much preservatives.

In an advantageous embodiment, the pouch composition further comprises a preservative in an amount of less than 0.5% by weight of the composition, such as less than 0.3% by weight of the composition, such as less than 0.15% by weight of the composition, such as less than 0.2% by weight of the composition, such as less than 0.1% by weight of the composition, such as free of preservative.

In an advantageous embodiment, the pouch composition further comprises a preservative in an amount of at least 0.05% by weight of the composition.

In an embodiment of the invention, the pouch composition comprises a preservative in an amount of 0.05 to 0.5% by weight of the pouch composition.

In an embodiment of the invention, the pouch composition comprises a preservative in an amount of 0.10 to 0.5% by weight of the pouch composition.

In an embodiment of the invention, the pouch composition comprises a preservative in an amount of 0.15 to 0.5% by weight of the pouch composition.

In an embodiment of the invention, the pouch composition comprises a preservative in an amount of 0.05 to 0.5% by weight of the pouch composition, such as 0.10 to 0.5% by weight of the pouch composition, such as 0.15 to 0.5% by weight of the pouch composition.

In an embodiment of the invention the pouch the composition comprises said sugar alcohol in an amount of 1-80% by weight of the pouch composition, such as 5-70% by weight of the pouch composition, such as 10-60% by weight of the pouch composition,
   and wherein the pouch composition comprises a preservative in an amount of 0.05 to 0.5% by weight of the pouch composition, such as 0.10 to 0.5% by weight of the pouch composition, such as 0.15 to 0.5% by weight of the pouch composition.

In an embodiment of the invention the pouch composition comprises sugar alcohol selected from the group consisting of sorbitol, erythritol, xylitol, lactitol, maltitol, mannitol, hydrogenated starch hydrolyzates, isomalt, or any combination thereof,
   wherein the composition comprises said sugar alcohol in an amount of 1-80% by weight of the pouch composition, such as 5-70% by weight of the pouch composition, such as 10-60% by weight of the pouch composition,
and wherein the pouch composition comprises a preservative in an amount of 0.05 to 0.5% by weight of the pouch composition, such as 0.10 to 0.5% by weight of the pouch composition, such as 0.15 to 0.5% by weight of the pouch composition.

In the above advantageous embodiment within the scope of the invention, the application of sugar alcohols may be allowed with even low amount of preservative and an optimal trigger for salivation and thereby release of composition and nicotine is obtained.

In an embodiment of the invention, the pouch composition comprises a preservative in an amount of 0 to 0.5% by weight of the pouch composition.

In an advantageous embodiment, the pouch composition is free of preservative.

In an advantageous embodiment, the preservative is selected from sorbic acid and its salts, benzoic acid and its salts, sulfur dioxide salts, nitrate salts, nitrite salts, acetic acid and its salts, lactic acid and its salts, malic acid and its salts.

Non-limiting examples of usable preservatives within the scope of the invention includes sorbic acid (E200) and salts thereof (e.g. sodium sorbate (E201), potassium sorbate (E202), calcium sorbate (E203)), benzoic acid (E210) and salts thereof (e.g. sodium benzoate (E211), potassium benzoate (E212), calcium benzoate (E213)), acetic acid (E260) and salts thereof (e.g. sodium acetate (E262), potassium acetate (E261), calcium acetate (E263)), lactic acid (E270), malic acid (E296), nitrite salts (sodium nitrite (E250), potassium nitrite (E249)), nitrate salts (sodium nitrate (E252), potassium nitrate (E252)), sulfur dioxide (E220) and sulfite salts (sodium sulfite (E221), potassium sulfite (E225), calcium sulfite (E226), sodium hydrogen sulfite (E222), sodium metabisulfite (E223), potassium metabisulfite (E224), calcium hydrogen sulfite (E227), potassium hydrogen sulfite (E228)).

In an advantageous embodiment, the heat-treated fibers are water-insoluble.

An advantage of the above embodiment may be that a very attractive soft, moist and moldable texture and mouthfeel are obtained due to a combination of sugar alcohol, water-insoluble fiber and water. The desirable texture and mouthfeel may be obtained while still being able to store manufactured pouches together in abutment e.g. in cans etc. without sticking too much together to result in ruptures of the pouches when being removed.

In an embodiment of the invention the pouch composition further comprises an amount of water-soluble. The water-soluble fibers may be intermixed with the water-insoluble fibers, e.g. when the source of fibers comprises a combination of water-soluble and water-insoluble fibers.

In an advantageous embodiment, the water-insoluble fiber is a plant fiber.

In an advantageous embodiment, the water-insoluble fiber is selected from wheat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, cellulose fibers, bran fibers, bamboo fibers, powdered cellulose, and combinations thereof.

Powdered cellulose within the scope of the invention is understood to be cellulose prepared by processing alpha-cellulose obtained as a pulp from strains of fibrous plant materials, such as wood pulp.

In an embodiment of the invention, the water-soluble fiber comprises or consists of cereal fibers.

In an embodiment of the invention, the water-soluble fiber comprises or consists of fruit and/or vegetable fibers.

In an advantageous embodiment of the invention, the water-insoluble composition comprises or consists of water-insoluble fiber selected from wheat fibers, oat fibers, pea fibers, powdered cellulose, or combinations thereof.

In an embodiment of the invention, the water-insoluble composition comprises or consists of water-insoluble fiber selected from wheat fibers, oat fibers, pea fibers, or combinations thereof.

In an embodiment of the invention, the water-insoluble composition comprises or consists of water-insoluble fiber selected from wheat fibers, oat fibers, or combinations thereof.

Non-limiting examples of usable water-insoluble fibers include VITACEL WF 600, VITACEL HF 600, VITACEL P95, VITACEL WF 200, VITACEL L 00, VITACEL Erbsenfaser EF 150, VITACEL bamboo fiberbaf 90, VITACEL HF 600, VITACEL Cellulose L700G, VITACEL PF200, VITACEL potatofiber KF200, VITACEL bamboo fiberhaf BAF40, VITACEL Haferfaser/oat fiber HF-401-30 US.

Non-limiting examples of usable powdered cellulose, include VITACEL LOO, VITACEL Cellulose L700G, VITACEL LC1000, VITACEL L600-20, VITACEL L600 etc.

In an embodiment, the powdered cellulose is chemically unmodified. Thus, powdered cellulose may be chemically unmodified cellulose fibers, which do not include e.g. microcrystalline cellulose (MCC).

In an advantageous embodiment, the water-insoluble fiber has a water binding capacity of at least 200%, such as at least 300%, such as at least 400%.

In an embodiment of the invention, the water-insoluble fiber has a water binding capacity of 200 to 1500%, such as 300 to 1500%, such as 400 to 1300%, such as 500 to 1200%, such as 500 to 1000%.

In an embodiment of the invention, the water-insoluble fiber has a water binding capacity of 200 to 1500%, such as 300 to 1300%, such as 300 to 900%, such as 300 to 700%, such as 400 to 700%.

In an embodiment of the invention, the water-insoluble fiber has a swelling capacity of at least 5.0 mL/g, such as 5.0-20 mL/g.

An advantage of the above embodiment is that the amount of water-insoluble fiber can be reduced without compromising the mouthfeel during use. If an amount of water-insoluble fiber is substituted for a water-soluble component, the swelling of the water-insoluble fiber will during use counteract the dissolution of the water-soluble component, thereby the user will not experience any decrease in pouch content during use.

In an advantageous embodiment of the invention, the water-insoluble composition comprises or consists of water-insoluble fiber in an amount between 5 and 50% by weight of the pouch composition and a water content of 15 to 70% by weight of said pouch composition.

In an advantageous embodiment, the pouch composition further comprises a pH-regulating agent, such as a basic pH-regulating agent, such as a basic buffering agent.

An advantage of the above embodiment may be that a longer shelf life may be obtained, by raising the pH in the pouch composition. At the same time, a more effective uptake of nicotine may be obtained, especially when using a basic (alkaline) pH regulating agent.

Another advantage of the above embodiment may be that a desirable mouthfeel may be obtained during use.

While lower amounts of pH regulating agent may be applicable in embodiments, e.g. by avoiding the use of nicotine salts, such as nicotine bitartrate, it may still be desirable to further increase the pH by adding pH regulating agent.

In an advantageous embodiment, the pouch composition comprises an alkaline buffering agent.

As used herein, the term alkaline buffering agent is used interchangeable with basic buffering agent, i.e. alkaline is used in the sense of "basic" as opposed to acidic.

In an advantageous embodiment, the pouch composition comprising pH-regulating agent in an amount of less than 6% by weight of the pouch composition, less than 5% by weight of the pouch composition, such as less than 4% by weight by weight of the pouch composition, such as less than 2% by weight by weight of the pouch composition, such as less than 1% by weight by weight of the pouch composition, such as free of pH-regulating agent.

In an embodiment of the invention, the pouch composition comprises pH-regulating agents in an amount of 0 to 6% by weight of the pouch composition, such as 0 to 5% by weight of the pouch composition, such as 0 to 4% by weight of the pouch composition, such as 0 to 3% by weight of the pouch composition, such as 0 to 2% by weight of the pouch composition such as 0 to 1% by weight of the pouch composition.

In an embodiment of the invention, the pouch composition comprises pH-regulating agents in an amount of 0.1 to 6% by weight of the pouch composition, such as in an amount of 0.1 to 5% by weight of the pouch composition, such as in an amount of 0.5 to 5% by weight of the pouch composition, such as in an amount of 0.5 to 4% by weight of the pouch composition, such as in an amount of 0.1 to 3% by weight of the pouch composition, such as in an amount of 0.1 to 2% by weight of the pouch composition, such as in an amount of 0.1 to 1% by weight of the pouch composition.

In an advantageous embodiment, the pouch composition is adapted to give a pH of at least 8.0, such as a pH of at least 9.0, when 2.0 gram of pouch composition is added to 20 mL of 0.02 M potassium dihydrogen phosphate-buffer (pH 7.4).

In an embodiment of the invention, the pouch composition is adapted to give a pH of at least 8.0, such as a pH of at least 8.2, such as a pH of at least 8.5, such as a pH of at least 8.7 such as a pH of at least 9.0, when 2.0 gram of pouch composition is added to 20 mL of 0.02 M potassium dihydrogen phosphate-buffer (pH adjusted to 7.4).

An advantage of the above embodiment may be that a relatively effective uptake of nicotine is facilitated due to the high pH value obtained.

A further advantage of the above embodiment may be that the need for preservative may be decreased or even eliminated and that low amounts of such preservatives may be used if not absent.

Also, the high pH value obtained may advantageously provide for a tingling sensation in the mouth which may be perceived as a desirable mouthfeel, e.g. due to resemblance with tobacco-based pouch products.

In an advantageous embodiment, the pH regulating agent is selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment, the pH regulating agent is a basic pH regulating agent, such as a basic buffering agent and/or such as Sodium carbonate, Sodium bicarbonate, Potassium carbonate, Potassium bicarbonate, Magnesium carbonate, or any combination thereof.

In an embodiment, xylitol, maltitol, mannitol, erythritol, isomalt, sorbitol, lactitol, and mixtures thereof may be used as the at least one sugar alcohol. The at least one sugar alcohol may also comprise further sugar alcohols. As an example embodiment, hydrogenated starch hydrolysates may be used, which comprises a mixture of sorbitol, maltitol and further sugar alcohols.

In an advantageous embodiment, the at least one sugar alcohol is selected from xylitol, maltitol, mannitol, erythritol, isomalt, sorbitol, lactitol, and mixtures thereof.

In an advantageous embodiment, the at least one sugar alcohol is selected from xylitol, maltitol, mannitol, erythritol, isomalt, lactitol, and mixtures thereof.

In an advantageous embodiment, the at least one sugar alcohol comprises xylitol and/or erythritol.

In an advantageous embodiment, the pouch composition comprises at least two alcohols.

It is noted that different sugar alcohols may be applied for the purpose of taste and salivation, where the sugar alcohol composition is made of different sugar alcohols having different properties with respect to storage, bacteria growth, processability and/or taste.

An even further advantage of the invention is that the combination of sugar alcohol, water-insoluble fiber and water provides not only an attractive mouthfeel but also a very attractive taste profile.

It is noted that a bulk density between 0.2 g/cm3 and 0.8 g/cm3, such as between 0.3 g/cm3 and 0.7 g/cm3, such as between 0.3 g/cm3 and 0.6 g/cm3, such as between 0.4 and 0.5 g/cm3 in relation to the composition including sugar alcohol in the amount of at least 1% by weight of the composition, such as at least 2% by weight of the composition, such as at least 5% by weight of the composition, such as at least 10% by weight of the composition does provide an attractive dissolving of the pouch content, including the nicotine, when put into contact with the mucosa.

In an embodiment of the invention, the at least two sugar alcohols are selected from xylitol, maltitol, mannitol, erythritol, isomalt, sorbitol, lactitol, and mixtures thereof.

In an advantageous embodiment, the pouch composition comprises the at least one sugar alcohol in an amount of at least 1% by weight of the composition, such as at least 2% by weight of the composition, such as at least 5% by weight of the composition, such as at least 10% by weight of the composition.

In an advantageous embodiment, the pouch composition comprises the at least one sugar alcohol in an amount of 1 to 80% by weight of the composition, such as 2 to 70% by weight of the composition, such as 5 to 60% by weight of the composition, such as 10 to 50% by weight of the composition.

In an embodiment of the invention the pouch composition comprises the at least one sugar alcohol in an amount of 5 to 40% by weight of the composition, such as 5-30% by weight of the composition.

In an advantageous embodiment, the at least one sugar alcohol comprises a DC (direct compressible) grade sugar alcohol.

In an advantageous embodiment, at least 50% by weight of the at least one sugar alcohol is a DC (direct compressible) grade sugar alcohol.

In an embodiment of the invention the sugar alcohol comprises a non-DC (non-direct compressible) grade sugar alcohol.

In an advantageous embodiment, the pouch composition comprises water in an amount of less than 60% by weight of the pouch composition, such as less than 50% by weight of the pouch composition, such as less than 40% by weight of the composition.

In an advantageous embodiment, the pouch composition comprises water in an amount of 8-65% by weight of the composition, such as 8-60% by weight of the composition, such as 8-50% by weight of the composition, such as 8-40% by weight of the composition, such as 20-40% by weight of the composition.

In an advantageous embodiment, the pouch composition comprises water in an amount of 10-40% by weight of the composition.

In an advantageous embodiment, the pouch composition comprises water in an amount of 20-65% by weight of the composition, such as 20-60% by weight of the composition, such as 20-50% by weight of the composition, such as 20-40% by weight of the composition.

In an advantageous embodiment, the pouch composition comprises water and water-insoluble fiber in a weight ratio of no more than 3.0, such as no more than 2.5, such as no more than 2.0, such as no more than 1.5, such as no more than 1.0.

In an embodiment, the pouch composition comprises water and water-insoluble fiber in a weight ratio of 3.0 to 0.2, such as 2 to 0,2, such as 2.0 to 1.0, such as 1.5 to 0.5.

Thus, the weight ratio above has in the numerator the content of water in percentage by weight of the pouch composition, and in the denominator the content water-insoluble fiber in percentage by weight of the pouch composition.

In an advantageous embodiment the pouch composition has a water activity of at least 0.6.

An advantage of the above embodiment may be that the product has a desirable soft, moist and moldable texture and mouthfeel.

A further advantage may be that the desirable soft, moist and moldable texture and mouthfeel are maintained/preserved during use as water in the form of saliva comes into contact with the pouch material.

A further advantage may be that the product has desirable moisture migrating properties allowing for a faster moist equilibrium in the mouth cavity providing a desirable texture and mouthfeel.

A further advantage may be that the product has desirable moisture migrating properties allowing for a faster moist equilibrium in the mouth cavity facilitating a faster onset of release of the water soluble pouch components such as nicotine, sugar alcohol and flavor.

In an embodiment of the invention, the pouch composition has a water activity of 0.6 to 0.8.

In an embodiment of the invention the pouch composition has a total aerobic microbial count (TAMC) of no more than $5 \times 10^3$ CFU/gram.

The content of aerobe microbials was determined according to method NMKL 86:2013 applying the colony forming unit method. The samples were grown for 3 days at 30 degrees Celsius. Number of living aerobe microorganism were counted per gram.

In an advantageous embodiment, the pouch composition has a growth of total aerobic microbial count (TAMC) of less than 50%, over a period of 3 months, when stored at 30 degrees Celsius.

In an embodiment of the invention the pouch composition has a total aerobic microbial count (TAMC) of 1 to $5 \times 10^3$ CFU/gram.

In an embodiment of the invention the pouch composition has a total yeast/mold count (TYMC) of no more than $2 \times 10^2$ CFU/gram.

The content of mold and yeast was determined according to method NMKL 98:2005 applying the colony forming unit method.

In an advantageous embodiment, the pouch composition has a growth of total yeast/mold count (TYMC) of less than 50%, over a period of 3 months, when stored at 30 degrees Celsius.

In an embodiment of the invention the pouch composition has a total yeast/mold count (TYMC) of 10 to $2 \times 10^2$ CFU/gram.

In an advantageous embodiment, the nicotine is selected from the group consisting of a nicotine salt, nicotine free base, nicotine bound to an ion exchanger, such as an ion exchange resin, such as nicotine polacrilex resin, a nicotine inclusion complex or nicotine in any non-covalent binding; nicotine bound to zeolites; nicotine bound to cellulose, such as microcrystalline cellulose, or starch microspheres, and mixtures thereof.

One example of a combination of different types of nicotine is the combination of free-base nicotine mixed with polacrilex resin, where some nicotine is be bound to the ion exchange resin, whereas some nicotine remains unbound.

Free base nicotine includes nicotine mixed with sugar alcohols, modified Calcium carbonate, water-soluble fibers, ion exchange resin, and combinations thereof. Nicotine bound to modified Calcium carbonate is described in international patent application WO 2010/121619, hereby incorporated by reference.

In an advantageous embodiment, the nicotine comprises non-salt nicotine.

In an advantageous embodiment, the nicotine comprises nicotine free base.

A very significant advantage of the above embodiment may be that a long shelf life of the pouched product may be obtained, with a long-life taste and texture. Providing nicotine in the free base form allows facilitates obtaining a higher pH in the pouch composition, without using too much alkaline pH adjusting agent.

Thus, in the above embodiment, the amount of alkaline pH adjusting agent may be reduced without compromising the shelf life and long-life taste and texture.

In an advantageous embodiment, the nicotine comprises nicotine mixed with ion exchange resin.

In an advantageous embodiment of the invention the nicotine comprises free-base nicotine mixed with ion exchange resin in a weight ratio between the free-base nicotine and the ion exchange resin of 0.1 to 2.0, preferably from 0.5 to 2.0, and most preferred about 0.67 to 1.0.

In an embodiment of the invention the nicotine comprises free-base nicotine mixed with ion exchange resin in a weight ratio between the free-base nicotine and the ion exchange resin of 1:1 to about 1:10, preferably from 1:2 to 1:6, and most preferred about 1:4-1:5.

Here, a weight ratio refers to the ratio of the mass of the first component divided by the mass of the second component. The term mixing ratio may also be used.

Thus, in the above embodiment, the nicotine comprises free-base nicotine mixed with ion exchange resin in a weight ratio between the free-base nicotine and the ion exchange resin of 0.1 to about 1, preferably from 0.17 to 0.5, and most preferred about 0.2-0.25.

In an embodiment, the pouch composition comprises water and water-insoluble fiber in a weight ratio of 0.2 to 0.8.

In an advantageous embodiment, the nicotine comprises a nicotine salt.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and hydrates thereof (e.g., nicotine zinc chloride monohydrate).

In an embodiment of the invention, the nicotine salt comprises or consists of nicotine bitartrate.

In an advantageous embodiment, the nicotine comprises nicotine bound to an ion exchange resin.

In an embodiment of the invention, the ion exchange resin is a polacrilex resin.

In an embodiment of the invention, the polacrilex resin is AMBERLITE®IRP64.

In an advantageous embodiment, the nicotine comprises synthetic nicotine.

In an advantageous embodiment, the nicotine comprised nicotine isolated from tobacco.

In an advantageous embodiment, the pouch composition comprises nicotine in an amount of at least 0.1% by weight, such as least 0.2% by weight of the pouch composition.

In an advantageous embodiment, the pouch composition comprises nicotine in an amount of 0.1 to 5.0% by weight of the pouch composition, such as 0.2 to 4.0% by weight of the pouch composition, such as 0.5 to 3.0% by weight of the pouch composition, such as 1.0 to 2.0% by weight of the pouch composition.

In an advantageous embodiment, the composition has a bulk density of at most 0.8 g/cm3, such as has a bulk density of at most 0.7 g/cm3, such as at most 0.6 g/cm3, such as at most 0.5 g/cm3.

An advantage of the above embodiment may be that a low-density composition may be obtained. Unexpectedly, the combination of water and sugar alcohols did not lead to a very dense and un-processable pouch composition but allowed a relatively light and low-density composition.

In an advantageous embodiment, the composition has a bulk density between 0.2 g/cm3 and 0.8 g/cm3, such as between 0.3 g/cm3 and 0.7 g/cm3, such as between 0.3 g/cm3 and 0.6 g/cm3, such as between 0.4 and 0.5 g/cm3.

In an advantageous embodiment, the pouch composition further comprises a humectant.

The humectant may attract and retain water in the oral cavity during use. However, the humectant may additionally moderate the release of nicotine, e.g. to facilitate a sustained release of nicotine.

In an advantageous embodiment of the invention, the pouch composition comprises humectant in an amount of 0.5 to 10% by weight of the pouch composition, such as in an amount of 0.5 to 5% by weight of the pouch composition, such as 1-3% by weight of the pouch composition.

In an embodiment, the humectant is selected from the list of glycerol, propylene glycol, alginate, modified starch, hydroxypropyl cellulose, triacetin, polyethylene glycol (PEG), pectin, xanthan gum, and combinations thereof.

In an embodiment, the humectant is or comprises alginate, such as sodium alginate, e.g. in an amount of 0.5% to 10% by weight of the pouch composition, such as 0.5 to 5% by weight of the pouch composition, such as 1-3% by weight of the pouch composition.

In an embodiment of the invention, the pouch composition further comprises glycerol.

In an embodiment of the invention, the pouch composition further comprises modified starch.

In an embodiment of the invention, the pouch composition further comprises hydroxypropyl cellulose (HPC).

In an advantageous embodiment, the pouch composition comprises a glidant, such as silicon dioxide, e.g. in an amount of between 0.5 and 5% by weight of the composition, such as between 1 and 3% by weight of the composition.

In an embodiment of the invention, the glidant is selected from talc powder, colloidal silica, silicon dioxide, corn starch, magnesium stearate, and combinations thereof.

In an advantageous embodiment, the pouch composition comprises flavor, e.g. in an amount of 0.01 and 15% by weight of the pouch composition.

In an embodiment of the invention, the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an alternative embodiment, the pouch composition is free of flavor.

In an embodiment of the invention, the pouch composition is free of preservatives and comprises pH-regulating agents in an amount of 0 to 6% by weight of the pouch composition.

In an embodiment of the invention, the pouch composition comprises the pH-regulating agent in an amount of less than 6% by weight of the pouch composition, less than 5% by weight of the pouch composition, such as less than 4% by weight by weight of the pouch composition, such as less than 2% by weight by weight of the pouch composition, such as less than 1% by weight by weight of the pouch composition, such as free of pH-regulating agent.

In an embodiment of the invention, the pouch composition is free of preservatives and comprises pH-regulating agents in an amount of 0 to 6% by weight of the pouch composition, such as 0 to 5% by weight of the pouch composition, such as 0 to 4% by weight of the pouch composition, such as 0 to 3% by weight of the pouch composition, such as 0 to 2% by weight of the pouch composition, such as 0 to 1% by weight of the pouch composition.

In an embodiment of the invention, the pouch composition comprises pH-regulating agents in an amount of 0.1 to 6% by weight of the pouch composition, such as in an amount of 0.1 to 5% by weight of the pouch composition, such as in an amount of 0.5 to 5% by weight of the pouch composition, such as in an amount of 0.5 to 4% by weight of the pouch composition, such as in an amount of 0.1 to 3% by weight of the pouch composition, such as in an amount of 0.1 to 2% by weight of the pouch composition, such as in an amount of 0.1 to 1% by weight of the pouch composition.

In an embodiment of the invention, the pouch composition is free of pH-regulating agents and free of preservatives.

In an embodiment of the invention, the pouch composition is free of pH regulating agent and comprises a preservative in an amount of 0 to 0.5% by weight of the pouch composition.

In an embodiment of the invention, the pouch composition is free of pH regulating agent and comprises a preservative in an amount of 0 to 0.5% by weight of the pouch composition, such as 0 to 0.4% by weight of the pouch composition, such as 0 to 0.3% by weight of the pouch composition, such as 0 to 0.2% by weight of the pouch composition, such as 0 to 0.1% by weight of the pouch composition.

In an embodiment of the invention, the pouch composition comprises nicotine free base, a preservative in an amount of 0 to 0.5% by weight of the pouch composition and a pH-regulating agents in an amount of 0 to 6% by weight of the pouch composition.

In an embodiment of the invention, the pouch composition comprises nicotine free base, a preservative in an amount of 0 to 0.5% by weight of the pouch composition and is free of pH regulating agent.

In an embodiment of the invention, the pouch composition comprises nicotine free base, a pH-regulating agent in an amount of 0 to 6% by weight of the pouch composition and is free of preservative.

In an embodiment of the invention, the pouch composition is free of tobacco, tobacco fibers and fibers derived from tobacco.

In some alternative embodiments, the pouch composition may comprise minor amounts of tobacco. Any, nicotine provided as part of tobacco, such as e.g. powdered tobacco, is further to the free-base nicotine. Such tobacco may e.g. be included to provide tobacco flavor.

In an embodiment, the pouch composition may comprise tobacco, tobacco fibers, or fibers derived from tobacco in an amount of 0.1 to 5.0% by weight of the pouch composition, such as in an amount of 0.1 to 3.0% by weight of the pouch composition. Thus, while the pouch composition in some embodiments may comprise small amounts of tobacco, this is in addition to the free-base nicotine, and thus the pouch composition is not tobacco based.

In an embodiment of the invention, the pouch composition comprises less than 5.0% by weight of tobacco, such as less than 3.0% by weight of the pouch composition, such as less than 1.0% by weight of the pouch composition, such as less than 0.5% by weight of the pouch composition, such as less than 0.1% by weight of the pouch composition, such as being free of tobacco.

In an advantageous embodiment of the invention, the pouch comprises a water-permeable membrane, comprising e.g. woven or non-woven fabric.

Typically, the pouch membrane comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch membrane having suitable opening dimensions in view of the pouch composition to be used, the material for the pouch membrane may be selected accordingly, e.g. comprising e.g. woven and/or non-woven fabric.

In other words, according to the various embodiments, the pouch membrane allows passage of saliva and prevents or inhibits passage of undissolved composition and the water-insoluble fibers. The pouch membrane may be of any suitable material e.g. woven or non-woven fabric (e.g. cotton, fleece etc.), heat sealable non-woven cellulose, such as long fiber paper, or other polymeric materials such as a synthetic, semi-synthetic or natural polymeric material. An example of suitable material for the pouch membrane is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

In more detail, regarding the material, the pouch membrane may be a natural, synthetic, semi-synthetic hydrophilic or hydrophobic membrane. It may be made from one or more biocompatible and physiologically acceptable polymeric material. Examples of suitable materials for the pouch membrane are cellulose acetate and derivatives thereof, carboxymethyl cellulose, polycellulose ester, other cellulose derivatives including ethylcellulose, propylcellulose, polyethylene, polypropylene, polystyrene, polyvinyl chloride, polyvinyl acetate, polymers of methacrylates and acrylates, natural rubber, polycarbonate, polyethylene terephthalate, polyester, polyamide and nylon. Other suitable materials are mentioned herein before.

Rayon fibers (i.e. regenerated cellulose), such as viscose rayon fibers may also be used, e.g. in combination with an acrylic polymer that acts as binder in the nonwoven material and provides for heat-sealing of the pouch membrane during manufacturing thereof. Other binders, such as one or more copolymers of vinyl acetate and acrylic acid ester, may also be used.

Suitable pouch membranes for are available under the trade names TABOKA, CATCH Dry, ETTAN, GENERAL, GRANIT, GOTEBORGS RAPE, GROV Snus White, METROPOL Kaktus, MOCCA Anis, MOCCA Mint, MOCCA Wintergreen, KICKS, PROBE, PRINCE, SKRUF, TRE ANKRARE, CAMEL Snus Original, CAMEL Snus Frost and CAMEL Snus Spice. The pouch membrane provides a liquid-permeable container of a type that may be considered to be similar in character to the mesh-like type of material that is used for the construction of a tea bag. Desired components of the nicotine composition to be released diffuse through the pouch membrane and into the mouth of the user.

Materials of the pouch membrane may have the form of a mesh, screen, perforated paper, permeable fabric, or the like. For example, pouch material manufactured from a mesh-like form of rice paper, or perforated rice paper, may dissolve in the mouth of the user. In some exemplary embodiments, the materials of the pouch membrane may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the nicotine contents permeates through the pouch material prior to the time that the pouch undergoes loss of its physical integrity. If desired, flavoring ingredients, disintegration aids, and other desired components, may be incorporated within, or applied to, the pouch material.

Examples of various types of pouch membrane materials set forth in U.S. Pat. No. 5,167,244 to Kjerstad. Fleece materials for use as pouch membranes are described e.g. in WO 2008/152469, GB 673,587, and EP 2 692 254.

In an advantageous embodiment of the invention, the pouch composition said composition comprises sugar alcohol selected from the group consisting of sorbitol, erythritol, xylitol, lactitol, maltitol, mannitol, hydrogenated starch hydrolyzates, isomalt, or any combination thereof and wherein the composition comprises said sugar alcohol in an amount of 1-80% by weight of the pouch composition, such as 5-70% by weight of the pouch composition, such as 10-60% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- and wherein said composition further comprises water-insoluble fibers in an amount of between 5 and 50% by weight of the pouch composition, such as between 10 and 30% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- and therein the water-insoluble composition comprises or consists of water-insoluble fiber, such as a water-insoluble plant fiber, such as wheat fibers, oat fibers, pea fibers, powdered cellulose, or combinations thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- and wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition and wherein the flavor is oil-based.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition,
- wherein said composition further comprises water-insoluble fibers in an amount of between 5 and 50% by weight of the pouch composition, such as between 10 and 30% by weight of the pouch composition,
- and wherein the pouch composition comprises a pH regulating agent selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof,
- wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent which is a basic pH regulating agent, such as a basic buffering agent and/or such as Sodium carbonate, Sodium bicarbonate, Potassium carbonate, Potassium bicarbonate, Magnesium carbonate, or any combination thereof.

In an embodiment of the invention the membrane comprises water insoluble fiber of different origin than the water insoluble fiber contained in the pouched product.

In an embodiment of the invention both the water insoluble fiber of the membrane and the water-insoluble fiber of the pouch composition comprises natural fiber.

In an embodiment of the invention both the water insoluble fibers of the membrane and the water-insoluble fibers of the pouch composition are natural fibers.

The invention further relates to a method for manufacturing an oral pouched product according to the invention or any of its embodiments, the method comprising the steps of adding the providing the pouch composition according to the invention or any of its embodiments, providing the saliva-permeable pouch, adding the pouch composition to said pouch, and sealing the pouch

DETAILED DESCRIPTION OF THE INVENTION

As used herein the term "nicotine" refers to nicotine used as a refined/isolated/purified/synthesized substance. Particularly, nicotine does not refer to tobacco materials having a content of nicotine.

As used herein the term "preservative" means antimicrobial agents, i.e. agents that kill or slow the growth of microbes. Microbes include yeast, mold, and bacteria. Thus, antioxidants are not preservatives.

As used herein the term "pouch composition" refers to the composition for use in an pouched product, i.e. in pouches for oral use comprising nicotine. Also, the terms "nicotine pouch composition" and "pouch composition" is used interchangeably.

As used herein the term "free-base nicotine" refers to non-protonated form of nicotine, and therefore does not include nicotine salts and nicotine provided as a complex between nicotine and an ion exchange resin. Nevertheless, the free-base nicotine may be mixed with an amount of ion exchange resin or water-soluble compositions such as sugar alcohols or water-soluble fibers. While free-base nicotine includes both free-base nicotine extracted from tobacco as well as synthetically manufactured free-base nicotine, the free-base nicotine is not provided in the form of tobacco or powdered tobacco. Typically, free-base nicotine is provided as a liquid.

As used herein the term "pouch" is intended to mean a container typically formed by a web of a fibrous material enclosing a cavity. The pouch is designed for administration of an active ingredient in the oral cavity, and thus it is adapted for oral use, it is non-toxic and not water-soluble. The fibrous material may e.g. form a woven or non-woven web or fabric. The pouch may for example be sealed by bonding two corresponding pieces of web or fabric to each other along their edges to form a cavity for the nicotine and the non-water-soluble composition. In order to release the nicotine, flavor and other water-soluble substances, the pouch is water-permeable so as to allow saliva from the oral cavity to penetrate the pouch and enter the cavity, where the saliva can come into contact with the nicotine, flavor and other water-soluble substances, whereby the nicotine, flavor and other water-soluble substances are released from the oral pouch.

As used herein the term "powder composition" refers to composition in the form of powder, i.e. as a particulate material having a relatively small particle size, for example between 1 and 1200 micrometer. Particularly, by powder composition is not meant a powdered tobacco.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include glycerol, propylene glycol, alginate, modified starch, hydroxypropyl cellulose, polyethylene glycol (PEG), triacetin, pectin, xanthan gum, etc.

As used herein the term "water-soluble" refers to a relatively high water-solubility, for example a water-solubility of more than 5 gram of water-soluble composition or substance per 100 mL of water measured at 25 degrees Celsius and pH of 7.0. When referring to a "soluble" composition or substance, water-soluble is meant, unless otherwise stated.

As used herein the term "water-insoluble" refers to relatively low water-solubility, for example a water-solubility of less than 0.1 gram of water-soluble composition or substance per 100 mL of water measured at 25 degrees Celsius and pH of 7.0. When referring to "insoluble", water-insoluble is meant unless otherwise stated.

As used herein the term "flavor" is understood as having its ordinary meaning within the art. Flavor includes liquid and powdered flavors. Thus, flavors do of course not include sweeteners (such as sugar, sugar alcohols and high intensity sweeteners), or acids providing pure acidity/sourness, nor compounds providing pure saltiness (e.g. NaCl) or pure bitterness. Flavor enhancers include substances that only provide saltiness, bitterness or sourness. Flavor enhancers thus include e.g. NaCl, Citric acid, ammonium chloride etc.

Typically, the pouches comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch having suitable opening dimensions in view of the pouch composition to be used, the material for the pouch may be selected accordingly, e.g. comprising e.g. woven and/or non-woven fabric.

In other words, according to the various embodiments, the pouch forms a membrane allowing passage of saliva and prevents or inhibits passage of undissolved composition and the water-insoluble fibers. The membrane of the pouch may be of any suitable material e.g. woven or non-woven fabric (e.g. cotton, fleece etc.), heat sealable non-woven cellulose or other polymeric materials such as a synthetic, semi-synthetic or natural polymeric material. An example of suitable pouch material is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

The pouch composition is filled into pouches and is maintained in the pouch by a sealing. An ideal pouch is chemically and physically stable, it is pharmaceutically acceptable, it is insoluble in water, it can be filled with powder and sealed, and it provides a semi-permeable membrane layer which prevent the powder from leaving the bag, but permit saliva and therein dissolved or sufficiently small suspended components from the pouch composition in the pouch, such as nicotine, to pass through said pouch.

The pouch may be placed in the oral cavity by the user. Saliva then enters into the pouch, and the nicotine and other components, which are soluble in saliva, start to dissolve and are transported with the saliva out of the pouch into the oral cavity, where the nicotine may be absorbed.

According to an embodiment of the invention, the pouch composition comprises one or more pH-regulating agent, such as a buffering agent.

In an embodiment of the invention, said pH-regulating agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

According to various embodiments of the invention, one or more sugar alcohols may be included in the pouch as part of the pouch composition, e.g. as a carrier or part thereof, as a humectant, or as a sweetener. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch composition comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch composition comprises sugar and/or sugarless sweeteners, e.g. sugar alcohol.

In an embodiment of the invention, the pouch composition comprises sugar and/or sugarless sweeteners in the amount of 1.0 to about 80% by weight of the pouch composition, more typically constitute 5 to about 70% by weight of the pouch composition, and more commonly 10 to 30% by weight of the pouch composition or 5 to 25% by weight of the pouch composition. In some other embodiments, the sugar and/or sugarless sweeteners constitute 10 to 60% by weight of the pouch composition or 10-50% by weight of the pouch composition. Sugar and/or sugarless sweeteners may function both as a sweetener and also as a humectant. In some embodiments, inclusion of certain ingredients may limit the about amounts of sugar and/or sugarless sweeteners further. In some embodiments, the content of sugar and/or sugarless sweeteners in the pouch composition is no more than 20% by weight of the pouch composition, such as no more than 15% by weight of the pouch composition, such as no more than 10% by weight of the pouch composition, such as no more than 5% by weight of the pouch composition.

The sweeteners may often support the flavor profile of the pouch composition.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In embodiments of the invention, the pouch composition further comprises water soluble fibers. Non-limiting examples of water-soluble fibers include inulin, polydextrose, and psyllium plant fibers. Other water-soluble dietary fibers may also be used.

In an embodiment of the invention the pouch composition comprises flavor. Flavor may typically be present in amounts between 0.01 and 15% by weight of the total composition of the pouch, such as between 0.01 and 5% by weight of the total composition.

In an alternative embodiment, the pouch composition is free of flavor.

Non-exhaustive examples of flavors suitable in embodiments of the present invention are coconut, coffee, chocolate, vanilla, citrus such as grape fruit, orange, lime, bergamot, or lemon, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, lemongrass, lime, jalapenos, chili (capsaicin), citrus, tobacco flavor, bergamot, smoky, dark & moldy, plum essence, and any combination thereof. The essential oils include peppermint, spearmint, menthol, eucalyptus, clove oil, bay oil, anise, thyme, cedar leaf oil, nutmeg, and oils of the fruits mentioned above.

In various embodiments of the invention, the pouch composition comprises a release controlling composition for controlling the release of the pouch composition and/or parts thereof, especially the nicotine.

The release controlling composition may, according to various embodiments, be selected from the group consisting of metallic stearates, modified calcium carbonate, hydrogenated vegetable oils, partially hydrogenated vegetable oils, polyethylene glycols, polyoxyethylene monostearates, animal fats, silicates, silicon dioxide, talc, magnesium stearates, calcium stearates, fumed silica, powdered hydrogenated cottonseed oils, hydrogenated vegetable oils, hydrogenated soya oil, emulsifiers, triglycerides, and mixtures thereof. Particularly, metallic stearates, such as magnesium stearate, may be advantageous.

The release controlling composition may be added to the pouch composition in various ways.

In an embodiment of the invention, the pouch composition is free of triglycerides.

For example, the release controlling composition may be added by full powder mixture during the last few minutes of the final mixing.

Alternatively, the release controlling composition may be added after granulation steps on a granulation premix.

Still further, the release controlling composition may be added only as a fraction of the pouch composition so two different release profiles of nicotine are achieved. Even further two or more fractions of the pouch composition may comprise different amounts of the release controlling composition, if any, thereby providing a more complex and tailored release profile of nicotine.

The release controlling composition, such as magnesium stearate, may have a sealing effect and can be used to control the release of the nicotine and the solubility of the pouch.

EXAMPLES

Example 1A—Preparation of Pouches Designed for Administration of Nicotine

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

Example 1B—Preparation of Pouches Designed for Administration of Nicotine

The material of the pouches is manufactured using rayon fibers, such as viscose rayon staple fibers. The pouch membrane is heat sealed along its edges except for an opening in one end into an inner cavity formed by the pouch membrane.

The powder is filled into pouches and is maintained in the pouch by a sealing.

Example 2A—Nicotine Premix I—Resin

A Stephan mixer (vacuum premixing) was charged with water, and nicotine was weighed and added, the mixer was closed and stirred for 5 minutes. Then ion exchange resin AMBERLITE® IRP64 was weighed and added to the mixer. The mixer was closed and stirred for 10-60 minutes.

Thereby, a mixture of nicotine and cation exchange resin was produced from the constituents stated in the below table 1.

TABLE 1

Ingredients used to manufacture nicotine premix I.

| Constituent | Amount (kg) | Amount (%) |
|---|---|---|
| Nicotine | 1.0 | 5.7 |
| Water | 12.5 | 71.4 |
| Resin | 4.0 | 22.9 |
| Total | 17.5 | 100.0 |

Nicotine:resin ratio: 1:4 (0.25)
% water in obtained nicotine-resin composition: 71.4

Example 2B—Nicotine Premix II—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 2.

TABLE 2

Ingredients used to manufacture nicotine premix II.

| Constituent | Amount (kg) | Amount (%) |
|---|---|---|
| Nicotine | 1.08 | 13.2 |
| Water | 2.80 | 34.1 |
| Resin | 4.32 | 52.7 |
| Total | 8.20 | 100.0 |

Nicotine:resin ratio: 1:4 (0.25)
% water in obtained nicotine-resin composition: 34.1
The total process time was 20 minutes.

Example 2C—Nicotine Premix III—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 3.

TABLE 3

Ingredients used to manufacture nicotine premix III.

| Constituent | Amount (kg) | Amount (%) |
|---|---|---|
| Nicotine | 1.08 | 18.5 |
| Water | 0.44 | 7.5 |
| Resin | 4.32 | 74.0 |
| Total | 5.84 | 100.0 |

Nicotine:resin ratio: 1:4 (0.25)
% water in obtained nicotine-resin composition: 7.5
The total process time was 20 minutes.

Example 2D—Nicotine Premix IV—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4.

TABLE 4

Ingredients used to manufacture nicotine premix IV.

| Constituent | Amount (kg) | Amount (%) |
|---|---|---|
| Nicotine | 1.08 | 10.0 |
| Water | 5.40 | 50.0 |
| Resin | 4.32 | 40.0 |
| Total | 10.8 | 100.0 |

Nicotine:resin ratio: 1:4 (0.25)
% water in obtained nicotine-resin composition: 50.0
The total process time was 20 minutes.

Example 2E—Nicotine Premix V—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4B

TABLE 4B

Ingredients used to manufacture nicotine premix V.

| Constituent | Amount (kg) | Amount (%) |
|---|---|---|
| Nicotine | 1.78 | 20.0 |
| Water | 2.80 | 31.5 |
| Resin | 4.32 | 48.5 |
| Total | 8.90 | 100.0 |

Nicotine:resin ratio: 1:2.43 (0.41)
% water in obtained nicotine-resin composition: 31.5
The total process time was 20 minutes.

Example 2F—Nicotine Premix VI—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4C.

TABLE 4C

Ingredients used to manufacture nicotine premix V.

| Constituent | Amount (kg) | Amount (%) |
|---|---|---|
| Nicotine | 3.05 | 30.0 |
| Water | 2.80 | 27.5 |
| Resin | 4.32 | 42.5 |
| Total | 10.17 | 100.0 |

Nicotine:resin ratio: 1:1.4 (0.71)
% water in obtained nicotine-resin composition: 27.5
The total process time was 20 minutes.

Example 2G—Nicotine Premix VII—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4D.

TABLE 4D

Ingredients used to manufacture nicotine premix V.

| Constituent | Amount (kg) | Amount (%) |
|---|---|---|
| Nicotine | 5.15 | 42.0 |
| Water | 2.80 | 22.8 |
| Resin | 4.32 | 35.2 |
| Total | 12.27 | 100.0 |

Nicotine:resin ratio: 1.19:1 (1.19)
% water in obtained nicotine-resin composition: 22.8
The total process time was 20 minutes.

Example 2H—Nicotine Premix VIII—Resin

A 60 liter planetary BEAR VARIMIXER mixer was charged with water, and nicotine was weighed and added. The mixer was stirred at low speed for 1 minute at ambient temperature. Then ion exchange resin AMBERLITE® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4E.

TABLE 4E

Ingredients used to manufacture nicotine premix V.

| Constituent | Amount (kg) | Amount (%) |
|---|---|---|
| Nicotine | 5.15 | 39.8 |
| Water | 2.80 | 21.6 |
| Resin | 4.32 | 33.4 |
| Pea fiber | 0.67 | 5.2 |
| Total | 12.94 | 100.0 |

Nicotine:resin ratio: 1.19:1 (1.19)
% water in obtained nicotine-resin composition: 21.6
The total process time was 20 minutes.

Example 3A—Pouches

Pouches PPC1-PPC5 containing nicotine premix are prepared comprising powdered compositions as outlined in table 5. The pouches are made as follows.

Fibers and water are mixed using a planetary BEAR VARIMIXER mixer for 5 minutes. Then, the following ingredients were added subsequently under continuous mixing: Nicotine premix (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch material of example 1, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

The pouches PPC6-PPC7 containing nicotine as nicotine salt or nicotine polacrilex resin as outlined in table 5. The pouches are made as follows.

Fibers and water are mixed using a planetary BEAR VARIMIXER mixer for 5 minutes. Then, the following ingredients were added subsequently under continuous mixing: first Nicotine bitartrate xH2O (NBT, nicotine content of 32.5%) or nicotine polacrilex resin (NPR, nicotine content of 15.9%) as applicable (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch material of example 1, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

TABLE 5

| | PPC1 | PPC2 | PPC3 | PPC4 | PPC5 | PPC6 | PPC7 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 25 | 15 | 10 | 40 | 30 | 30 |
| Raw material | Content in weight percent | | | | | | |
| NPR | — | — | — | — | — | — | 12.1 |
| NBT | — | — | — | — | — | 5.9 | — |
| Nicotine premix II | 14.6 | 14.6 | 14.6 | 14.6 | 14.6 | — | — |
| Xylitol | 11.3 | 16.3 | 26.3 | 31.3 | 1.3 | 15.0 | 8.8 |
| Purified water | 25 | 20 | 10 | 5 | 35 | 30 | 30 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 8.9 | 8.9 | 8.9 | 8.9 | 8.9 | 8.9 | 8.9 |
| NaCl | 0.1 | 0.1 | 0.1 | 0.1 | 0.1 | 0.1 | 0.1 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premix II (example 2B) comprises 34.1 wt % water, thereby contributing to the total water content.

Pouch content: 500 mg total, i.e. nicotine conc 19.2 mg/g

The Xylitol applied is e.g. trade name "XYLITAB 200".

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, bran fibers, bamboo fibers, powdered cellulose, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC1-PPC5 show that different pouches having a water content of at least 10% by weight of the pouch composition can be made using free-base nicotine. Pouches PPC6 and PPC7 have a similar water content as PPC1, but uses nicotine salt and nicotine in complex with an ion exchange resin.

Example 3B—Pouches

Pouches PPC11-PPC15 containing nicotine premix are prepared comprising powdered compositions as outlined in table 6. The pouches are made as follows.

Fibers and powder ingredients (except glidants) are mixed using a planetary BEAR VARIMIXER mixer for 2 minutes. Then, Nicotine premix is added and mixed for 2 minutes. Water is then added and mixed for 5 minutes followed by liquid flavor (if any—mixed for 1 minute) and glidant (if any—mixed for 1 minute). The total mixing time is 9-11 minutes.

Comp. NN1-NN2 are made similar to pouches PPC11-PPC15, only of course without adding nicotine premix.

TABLE 6

| | PPC 11 | PPC 12 | PPC 13 | PPC 14 | PPC 15 | Comp. NN1 | Comp. NN2 |
|---|---|---|---|---|---|---|---|
| Amount of nicotine | 9.6 mg | 9.6 mg | 9.6 mg | 9.6 mg | 9.6 mg | — | — |
| Water content [wt %] | 30 | 25 | 15 | 10 | 35 | 30 | 30 |
| Raw material | Content in weight percent | | | | | | |
| Nicotine premix II | 14.6 | 14.6 | 14.6 | 14.6 | 14.6 | — | — |
| Isomalt | 11.3 | 22.3 | 44.3 | 55.3 | 0.3 | 20.9 | 20.9 |
| Purified water | 25 | 20 | 10 | 5 | 30 | 30 | 30.1 |
| Wheat fiber | 30 | 24 | 12 | 6 | 36 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 9.0 | 9.0 | 9.0 | 9.0 | 9.0 | 8.9 | 8.9 |
| NaCl | — | — | — | — | — | 0.1 | 0.1 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | — |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premix II comprises 34.1 wt % water, thereby contributing to the total water content.

Pouch content: 500 mg total.

The applied Isomalt e.g. GALENIQ 720.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, bran fibers, bamboo fibers, powdered cellulose, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC11-PPC15 shows varying water content of at least 10% by weight of the pouch composition. The water content varies, but the ratio between the amount of added purified water and the amount of fibers remain constant. Comparative pouches Comp.NN1-NN2 are free of nicotine.

Example 3C—Pouches

Pouches PPC21-PPC27 are prepared comprising powdered compositions as outlined in table 7 and are made similarly to pouches PPC11-PPC15 of example 3B.

TABLE 7

| | PPC 21 | PPC 22 | PPC 23 | PPC 24 | PPC 25 | PPC 26 | PPC 27 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix II | 14.6 | 7.3 | 14.6 | 14.6 | 14.6 | 14.6 | 14.6 |
| Liquid nicotine* | — | 1.0 | — | — | — | — | — |
| Xylitol | 11.3 | 15.1 | 16.3 | 13.3 | 11.4 | 9.4 | 16.4 |
| Purified water | 25 | 27.5 | 25 | 25 | 25 | 25 | 25 |
| MCC (Avicel 102) | 30 | — | — | — | — | — | — |
| Wheat fiber | — | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | — | 3.0 | 5.0 | 7.0 | — |
| Flavor | 9.0 | 9.0 | 9.0 | 9.0 | 9.0 | 9.0 | 9.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | — | — | — |
| Silicon dioxide | 2.0 | 2.0 | 2.0 | 2.0 | 2.0 | 2.0 | 2.0 |
| Total | 100 | 100 | 100 | 100 | 100 | 100 | 100 |

*Liquid nicotine is added as a nicotine-sugar alcohol premix in powder form. The nicotine premix II comprises 34.1 wt % water, thereby contributing to the total water content.

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, bran fibers, bamboo fibers, powdered cellulose, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC21 shows the use of e.g. microcrystalline cellulose (MCC) instead of wheat fibers.

Pouch PPC22 shows the use of a combination of nicotine-ion exchange resin premix and nicotine-sugar alcohol premix.

Pouches PPC23-PPC26 shows the use of different amounts of buffering agent (here sodium carbonate). For high amounts of basic buffering agents, achieving a more alkaline environment, there is less need for a preservative (here potassium sorbate), therefore it is omitted in PPC25-PPC26, having the highest amounts of alkaline buffering agents.

Pouch PPC27 is free of preservative and buffering agent.

Example 3D—Pouches

Pouches PPC31-PPC32 are prepared comprising powdered compositions as outlined in table 8 and are made similarly to pouches PPC1-PPC5 of example 3A, but using nicotine premix I and III, respectively.

Pouches PPC33-PPC37 are made as described below.

The nicotine and sugar alcohol (xylitol, sorbitol, maltitol or other) are weighed. The nicotine is slowly added to the sugar alcohol powder under stirring (KITCHENAID mixer operated at about 30 RPM in about 30 minutes). The resulting granulate is sieved and placed on a tray. The resulting powder is dried at ambient temperature overnight and is thereafter sieved to obtain a nicotine-sugar alcohol premix. It is also possible to add an amount of water to the nicotine before mixing with the sugar alcohol. Any such water will then be evaporated during the drying.

Fibers and water are mixed using a planetary BEAR VARIMIXER mixer for 5 minutes. Then, the following ingredients were added subsequently under continuous mixing: Powder ingredients other than nicotine premix (mixed for 2 minutes), nicotine-sugar alcohol premix (mixed for 2 minutes), then liquid flavor if any (mixed for 1 minute) and finally glidant if any (mixed for 1 minute). The total mixing time is 9-11 minutes.

The final powder composition is filled into pouches (target fill weight 500 mg powder per pouch). The pouch material of example 1, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

TABLE 8

| | PPC | | | | | | |
|---|---|---|---|---|---|---|---|
| | PPC 31 | PPC 32 | PPC 33 | PPC 34 | PPC 35 | PPC 36 | PPC 37 |
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix I | 33.7 | — | — | — | — | — | — |
| Nicotine premix III | — | 10.4 | — | — | — | — | — |
| Liquid nicotine* | — | — | 1.9 | 1.9 | 1.9 | 1.9 | 1.9 |
| Isomalt | 11.2 | 11.3 | 19.0 | — | — | — | — |
| Sorbitol | — | — | — | 19.0 | — | — | — |
| Maltitol | — | — | — | — | 19.0 | — | — |
| Inulin | — | — | — | — | — | 19.0 | — |
| Polydextrose | — | — | — | — | — | — | 19.0 |
| Purified water | 6 | 29.2 | 30 | 30 | 30 | 30 | 30 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |

TABLE 8-continued

| Sodium carbonate | 5.0 | 5.0 | 5.0 | 5.0 | 5.0 | 5.0 | 5.0 |
|---|---|---|---|---|---|---|---|
| Flavor | 9.0 | 9.0 | 9.0 | 9.0 | 9.0 | 9.0 | 9.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

*Liquid nicotine is added as a nicotine-sugar alcohol premix or as a nicotine-water-soluble fiber premix in powder form. The nicotine premix I comprises 71.4 wt % water, thereby contributing to the total water content. The nicotine premix II comprises 34.1 wt % water, thereby contributing to the total water content. The nicotine premix III comprises 7.5 wt % water, thereby contributing to the total water content.

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, bran fibers, bamboo fibers, powdered cellulose, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC31-PPC32 show use of other nicotine pre-mixes.

Pouches PPC33-PPC35 show use of nicotine pre-mixed with different sugar alcohol.

Pouches PPC36-PPC37 show use of nicotine pre-mixed with different water-soluble fibers.

Example 3E—Pouches

Pouches PPC41-PPC46 are prepared comprising powdered compositions as outlined in table 9 and are made similarly to pouches PPC1-PPC5 of example 3A.

TABLE 9

| | PPC | | | | | |
|---|---|---|---|---|---|---|
| | PPC 41 | PPC 42 | PPC 43 | PPC 44 | PPC 45 | PPC 46 |
| Amount of nicotine | 4.8 mg | 7.2 mg | 9.6 mg | 12 mg | 9.6 mg | 9.6 mg |
| Water content [wt %] | 27.5 | 28.3 | 30 | 31.2 | 30 | 30 |

TABLE 9-continued

| Raw material | Content in weight percent | | | | | |
|---|---|---|---|---|---|---|
| Nicotine premix II | 7.3 | 9.7 | 14.6 | 18.3 | 14.6 | 14.6 |
| Xylitol | 18.6 | 16.2 | 11.3 | 7.6 | 13.3 | 5 |
| Erythritol | — | — | — | — | — | 6.3 |
| Purified water | 25 | 25 | 25 | 25 | 25 | 25 |
| Wheat fiber | 30 | 30 | 30 | 30 | 30 | 30 |
| Sodium alginate | 2.0 | 2.0 | 2.0 | 2.0 | — | 2.0 |
| Sodium carbonate | 5.0 | 5.0 | 5.0 | 5.0 | 5.0 | 5.0 |
| Flavor | 9.0 | 9.0 | 9.0 | 9.0 | 9.0 | 8.9 |
| NaCl | — | — | — | — | — | 0.1 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premix II comprises 34.1 wt % water, thereby contributing to the total water content.

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, bran fibers, bamboo fibers, powdered cellulose, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC41-PPC44 show use of different doses of nicotine, from 4.8 mg to 12 mg.

Pouch PPC45 shows pouch without alginate, otherwise comparable to pouch PPC43. Pouch PPC46 shows a pouch with a combination of two sugar alcohols.

Example 3F—Pouches

Pouches PPC51-PPC53 are prepared comprising powdered compositions as outlined in table 10 and are made as follows.

Fibers and powder ingredients (except nicotine containing powders and glidants) are mixed for 1 minute using a planetary BEAR VARIMIXER mixer. Then, NPR and NBT is added and mixed for 2 minutes (if applicable). Nicotine premix is then added and mixed for 2 minutes. Subsequently, water is added and mixed for 5 minutes followed by liquid flavor (if any—mixed for 1 minute) and glidant (if any—mixed for 1 minute). The total mixing time is 9-11 minutes.

TABLE 10

The nicotine premix II comprises 34.1 wt % water, thereby contributing to the total water content

| | PPC | | |
|---|---|---|---|
| | PPC51 | PPC52 | PPC53 |
| Amount of nicotine | 9.6 mg | 9.6 mg | 9.6 mg |
| Water content [wt %] | 30 | 30 | 30 |
| Raw material | Content in weight percent | | |
| NPR | — | 6.0 | 3.0 |
| NBT | 2.9 | — | 1.5 |
| Nicotine premix II | 7.3 | 7.3 | 7.3 |
| Isomalt | 15.2 | 12.1 | 13.6 |
| Purified water | 27.5 | 27.5 | 27.5 |
| Wheat fiber | 30 | 30 | 30 |
| Sodium carbonate | 5.0 | 5.0 | 5.0 |
| Flavor | 9.0 | 9.0 | 9.0 |
| High intensity sweetener | 1.0 | 1.0 | 1.0 |
| Potassium sorbate | 0.1 | 0.1 | 0.1 |
| Silicon dioxide | 2.0 | 2.0 | 2.0 |
| Total | 100 | 100 | 100 |

Pouch content: 500 mg total

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, bran fibers, bamboo fibers, powdered cellulose, cocoa fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC51 shows pouch using nicotine-ion exchange resin premix in combination with nicotine bitartrate (NBT).

Pouch PPC52 shows pouch using nicotine-ion exchange resin premix in combination with nicotine polacrilex resin (NPR).

Pouch PPC53 shows pouch using nicotine-ion exchange resin premix in combination with nicotine bitartrate (NBT) and nicotine polacrilex resin (NPR).

Example 3G—Pouches

Pouches PPC61-PPC65 containing nicotine premix are prepared comprising powdered compositions as outlined in table 10A. The pouches are made as follows.

Fibers and powder ingredients (except glidants) are mixed using a LOEDIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

TABLE 10A

| | PPC 61 | PPC 62 | PPC 63 | PPC 64 | PPC 65 | PPC 66 | PPC 67 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix VI | 6.4 | 6.4 | 6.4 | 6.4 | 6.4 | 6.4 | 6.4 |
| Xylitol | 5 | 18.3 | 18.3 | 18.3 | 5 | 5 | 5 |
| Erythritol | 13.5 | — | — | — | 13.5 | 13.5 | 13.5 |
| Purified water | 28 | 28 | 28 | 28 | 28 | 28 | 28 |
| Wheat fiber | 30 | 30 | 20 | 40 | 30 | 30 | 30 |
| Sodium alginate | 2.0 | 2.0 | 2.0 | 2.0 | 2.0 | — | — |
| Glycerol | — | — | — | — | — | 2.0 | — |
| Hydroxypropyl cellulose | — | — | — | — | — | — | 2.0 |
| Sodium carbonate | 5.0 | 3.0 | 3.0 | 3.0 | 3.0 | 3.0 | 3.0 |
| Sodium bicarbonate | — | 2.0 | 2.0 | 2.0 | 2.0 | 2.0 | 2.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premix VI comprises 27.5 wt % water, thereby contributing to the total water content.

Pouch content: 500 mg total.

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, powdered cellulose, cocoa fibers, bamboo fibers, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC61-PPC62 show use of different sweetener and buffer combinations.

Pouches PPC63-PPC64 show pouches with varying fiber content.

Pouches PPC65-PPC67 show use of different humectants.

Example 3H—Pouches

Pouches PPC71-PPC76 containing nicotine premix are prepared comprising powdered compositions as outlined in table 10B. The pouches are made as follows.

Fibers and powder ingredients (except glidants) are mixed using a LOEDIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1, made from long fiber paper, is used. The powder is filled into pouches and is maintained in the pouch by a sealing.

TABLE 10B

| | PPC 71 | PPC 72 | PPC 73 | PPC 74 | PPC 75 | PPC 76 | PPC 77 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix IV | 19.2 | — | — | — | — | — | — |
| Nicotine premix V | — | 9.6 | — | — | — | — | — |
| Nicotine premix VI | — | — | — | — | 6.4 | 6.4 | 6.4 |
| Nicotine premix VII | — | — | 4.6 | — | — | — | — |
| Nicotine premix VIII | — | — | — | 4.8 | — | — | — |
| Purified water | 21 | 27 | 29 | 29 | 28 | 28 | 28 |
| Wheat fiber | 30 | 30 | 30 | 29.75 | — | — | — |
| Oat fiber | — | — | — | — | 30 | — | — |
| Pea fiber | — | — | — | 0.25 | — | 30 | — |
| Powdered cellulose | — | — | — | — | — | — | 30 |
| Xylitol DC | 5.0 | 5.0 | 5.0 | 5.0 | 5.0 | 5.0 | 5.0 |
| Erythritol | 7.7 | 11.3 | 14.3 | 14.1 | 13.5 | 13.5 | 13.5 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premixes comprise water in varying amount, thereby contributing to the total water content.

Nicotine premix VIII comprises peafiber.

Pouch content: 500 mg total, i.e. nicotine conc 19.2 mg/g

Wheat fiber, trade name "VITACEL 600 WF plus".

Powdered cellulose, trade name "VITACEL LOO" or "VITACEL L700G".

Oat fiber, trade name "VITACEL HF 600".

Pea fiber, trade name "VITACEL EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, bamboo fibers, powdered cellulose, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC71-PPC74 show use of different nicotine premixes.

Pouches PPC75-PPC77 show use of different fibers.

Example 3I—Pouches

Pouches PPC81-PPC92 containing nicotine premix are prepared comprising powdered compositions as outlined in table 100. The pouches are made as follows.

Fibers and powder ingredients (except glidants) are mixed using a LOEDIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1, made from long fiber paper, is used. The powder is filled into pouches and is maintained in the pouch by a sealing.

TABLE 10C I/II.

| | PPC | | | | | | | |
|---|---|---|---|---|---|---|---|---|
| | PPC 81 | PPC 82 | PPC 83 | PPC 84 | PPC 85 | PPC 86 | PPC 87 | PPC 88 |
| Amount of nicotine | 9.6 mg | 9.6 mg | 9.6 mg | 9.6 mg | 9.6 mg | 9.6 mg | 9.6 mg | 9'6 mg |
| Water content [wt %] | 30 | 30 | 30 | 30 | 30 | 30 | 30 | 30 |
| Raw material | Content in weight percent | | | | | | | |
| Nicotine premix II | 14.6 | 14.6 | 14.6 | 14.6 | — | — | — | — |
| Nicotine premix VI | — | — | — | — | 6.4 | 6.4 | 6.4 | 6.4 |
| Purified water | 25 | 25 | 25 | 25 | 28 | 28 | 28 | 28 |
| Wheat fiber | 30 | — | — | — | — | — | — | 15 |
| Oat fiber | — | 30 | — | — | 15 | — | — | — |
| Pea fiber | — | — | 30 | — | — | 15 | — | — |
| Powdered cellulose | — | — | — | 30 | — | — | 15 | — |
| Xylitol DC | 5.0 | 5.0 | 5.0 | 5.0 | 5.0 | 5.0 | 5.0 | 5.0 |
| Erythritol | 8.3 | 8.3 | 8.3 | 8.3 | 28.5 | 28.5 | 28.5 | 28.5 |
| Sodium alginate | 2.0 | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 | 2.0 |
| Total | 100 | 100 | 100 | 100 | 100 | 100 | 100 | 100 |

TABLE 10C II/II

| | PPC | | | | | |
|---|---|---|---|---|---|---|
| | PPC 89 | PPC 90 | PPC 91 | PPC 92 | PPC 93 | PPC 94 |
| Amount of nicotine | 9.6 mg | 9.6 mg | 9.6 mg | 9.6 mg | 9.6 mg | 9.6 mg |
| Water content [wt %] | 30 | 30 | 30 | 30 | 30 | 30 |
| Raw material | Content in weight percent | | | | | |
| Nicotine premix II | 14.6 | 14.6 | 14.6 | 14.6 | — | — |
| Nicotine premix VI | — | — | — | — | 6.4 | 6.4 |
| Purified water | 25 | 25 | 25 | 25 | 28 | 28 |
| Wheat fiber | 15 | — | — | — | 15 | 15 |
| Oat fiber | — | 15 | — | — | — | — |
| Pea fiber | — | — | 15 | — | — | — |
| Powdered cellulose | — | — | — | 15 | — | — |
| Xylitol DC | 5.0 | 5.0 | 5.0 | 5.0 | 5.0 | 5.0 |
| Erythritol | 23.3 | 23.3 | 23.3 | 23.3 | 28.5 | 20.5 |
| Sodium alginate | 2.0 | 2.0 | 2.0 | 2.0 | | |
| NaCl | — | — | — | — | — | 10 |
| Sodium carbonate | 5.0 | 5.0 | 5.0 | 5.0 | 3.5 | 5.0 |
| Sodium bicarbonate | — | — | — | — | 3.5 | — |
| Flavor | 7.0 | 7.0 | 7.0 | 7.0 | 7.0 | 7.0 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premixes comprise water in varying amount, thereby contributing to the total water content.

Pouch content: 500 mg total, i.e. nicotine conc 19.2 mg/g

Wheat fiber, trade name "VITACEL 600 WF plus" or "VITACEL 200WF".

Powdered cellulose, trade name "VITACEL LOO" or "VITACEL L700G".

Oat fiber, trade name "VITACEL HF 600".

Pea fiber, trade name "VITACEL EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, apple fibers, cocoa fibers, bamboo fibers, powdered cellulose, bran fibers, and cellulose fiber.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC81-PPC92 shows the use of different fibers, in different amounts and with different nicotine premixes.

Example 3J—Pouches

Pouches PPC101-PPC103 and COMP.P1 and COMP.P2 containing nicotine premix are prepared comprising powdered compositions as outlined in table 10D. The pouches are made as follows.

Fibers and powder ingredients (except glidants) are mixed using a LOEDIGE mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1, made from long fiber paper, is used. The powder is filled into pouches and is maintained in the pouch by a sealing.

TABLE 10D

|  | PPC | | | | |
| --- | --- | --- | --- | --- | --- |
|  | COMP. P1 | PPC 101 | COMP. P2 | PPC 102 | PPC 103 |
| Amount of nicotine | 9.6 mg | 9.6 mg | 9.6 mg | 9.6 mg | 9.6 mg |
| Water content [wt %] | 48 | 38 | 51 | 41 | 31 |
| Raw material | Content in weight percent | | | | |
| Nicotine premix II | 14.6 | 14.6 | 14.6 | 14.6 | 14.6 |
| Purified water | 43 | 33 | 43 | 33 | 23 |
| Wheat fiber | 35.4 | 35.4 | — | — | — |
| MCC (Avicel PH-102) | — | — | 35.4 | 35.4 | 35.4 |
| Erythritol | — | 10 | — | 10 | 20 |
| Sodium carbonate | 1.5 | 1.5 | 1.5 | 1.5 | 1.5 |
| NaCl | 3.5 | 3.5 | 3.5 | 3.5 | 3.5 |
| Liquid flavor composition | 1.0 | 1.0 | 1.0 | 1.0 | 1.0 |
| Sesame oil | 1.0 | 1.0 | 1.0 | 1.0 | 1.0 |
| Total | 100 | 100 | 100 | 100 | 100 |

Pouch content: 500 mg total, i.e. nicotine concentration 19.2 m g/g

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Example 3K—Pouches

Pouches PPC111-PPC117 containing nicotine premix are prepared comprising powdered compositions as outlined in table 10E. The pouches are made as follows.

Powdered ingredients including powdered flavor (if any) are mixed using a planetary BEAR VARIMIXER mixer for 2 minutes. Then, the nicotine is added and mixed for 2 minutes. Then water is slowly added while the mixer is running, followed by addition of liquid flavor. Finally, silicon dioxide is added and the mixed for about 1 minute. The total mixing time is about 30 minutes.

The final powder composition is filled into pouches (target fill weight 500 mg powder per pouch). The pouch material of example 1, made from long fiber paper, is used. The powder is filled into pouches and is maintained in the pouch by a sealing.

The material of the pouches is heat sealable non-woven cellulose, such as long fiber paper. Pouches that are not in form of non-woven cellulose fabric may also be used according to the invention.

The powder is filled into pouches and is maintained in the pouch by a sealing.

TABLE 10E

|  | PPC | | | | | | |
| --- | --- | --- | --- | --- | --- | --- | --- |
|  | PPC 111 | PPC 112 | PPC 113 | PPC 114 | PPC 115 | PPC 116 | PPC 117 |
| Amount of nicotine | 9.6 mg | 9.6 mg | 9.6 mg | 9.6 mg | 9.6 mg | 9.6 mg | 9.6 mg |
| Water content [wt %] | 15 | 30 | 45 | 30 | 30 | 30 | 30 |
| Density (gram per Liter) | 256 | 303 | 578 | ND | ND | ND | ND |
| Hausner ratio | 1.25 | 1.22 | 1.11 | ND | ND | ND | ND |
| Raw material | Content in weight percent | | | | | | |
| Nicotine premix II | 14.6 | 14.6 | 14.6 | 14.6 | 14.6 | 14.6 | 14.6 |
| Sugar alcohol(s) | 12.3 | 12.3 | 12.3 | 12.4 | 12.7 | 12.1 | 11.9 |
| Purified water | 10 | 25 | 40 | 25 | 25 | 25 | 25 |
| Wheat fiber | 45 | 30 | 15 | 30 | 30 | 30 | 30 |
| Sodium alginate | 2.0 | 2.0 | 2.0 | 2.0 | 2.0 | 2.0 | 2.0 |
| Sodium carbonate | 4.0 | 4.0 | 4.0 | 4.0 | 4.0 | 4.0 | 4.0 |
| Flavor | 9.0 | 9.0 | 9.0 | 9.0 | 9.0 | 9.0 | 9.0 |
| High intensity sweetener | 1.0 | 1.0 | 1.0 | 1.0 | 1.0 | 1.0 | 1.0 |

TABLE 10E-continued

| | | | | | | | |
|---|---|---|---|---|---|---|---|
| Potassium sorbate | 0.1 | 0.1 | 0.1 | 0.01 | 0.05 | 0.2 | 0.5 |
| Silicon dioxide | 2.0 | 2.0 | 2.0 | 2.0 | 2.0 | 2.0 | 2.0 |
| Total | 100 | 100 | 100 | 100 | 100 | 100 | 100 |

The nicotine premix II comprises 34.1 wt % water, thereby contributing to the total water content.

Pouch content: 500 mg total, i.e. nicotine concentration 19.2 m g/g

The sugar alcohol(s) may be Xylitol e.g. trade name "XYLITAB 200" and/or Isomalt e.g. tradename "GALENIQ 720".

Wheat fiber, trade name "VITACEL 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, cellulose fibers, bran fibers, bamboo fibers, powdered cellulose, apple fibers, cocoa fibers, and cellulose fiber.

For example, a mixture of e.g. menthol and peppermint may be used. Of course, other flavors as described herein may be use as well, in combination with menthol and/or peppermint or replacing these.

Sodium alginate, glycerol and hydroxypropyl cellulose (HPC) may be used as humectants. Other humectants as described herein may also be used in combination with sodium alginate, glycerol or HPC or as an alternative.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC111-PPC113 show pouches having different water and water-insoluble fiber contents.

PPC114-117 show varying amount of preservative.

Example 4—Evaluation

The produced pouches of the invention were evaluated and found highly suitable as delivery vehicles of nicotine in that they provide a favorable release of nicotine and at the same time are pleasant to the user, e.g. with respect to a desirable soft, moist and moldable texture. In particular, the pouches of the invention did not need any wetting before use as opposed to conventional nicotine pouches with low moisture content which may feel dry initially in use.

Example 5—Shelf Life

The pouch products PPC1 and PPC46 were compared to the Comp. NN1 and NN2 pouch with respect to shelf life.

Evaluation of shelf life is performed as described in the following.

Samples of the pouched products PPC1 and PPC46 were kept at 25 degrees Celsius for 3 months in sealed containers. Then, the pouched products were visually inspected for microbial growth.

Further, 6 batches of pouch composition PPC1 were tested for selected microbes.

TABLE 11

Measured microbial content for a selected pouched product.

| | PPC1 |
|---|---|
| Total aerobic microbial count (TAMC) | <10 CFU/g |
| Total yeast/mold count (TYMC) | <100 CFU/g |

The content of aerobe microbials (TAMC) was determined according to method NMKL 86:2013 applying the colony forming unit method. The samples were grown for 3 days at 30 degrees Celsius. Number of living aerobe microorganism were counted per gram.

The content of mold and yeast (TYMC) was determined according to method NMKL 98:2005 applying the colony forming unit method.

The tested content of aerobe microbials and content of mold and yeast was within desired limits allowing for a product with preserved visual appearance, taste and mouthfeel. The pouched products PPC1 and PPC46 were found to have a visual appearance that was markedly better than Comp. NN2 and also having significant lower content of tested microbes.

Example 6—User Evaluation

The pouch product PPC1 was evaluated with respect to perceived effect from nicotine and with respect to burning (tingling) sensation.

Evaluation of perceived effect from nicotine and burning (tingling) sensation is performed as described in the following.

Perceived effect from nicotine and burning (tingling) sensation was evaluated by a test panel of 4 trained assessors. Each assessor evaluates all samples twice. Average evaluations are estimated.

The pouch product PPC1 was evaluated to have a fast onset of action and a high perceived effect from nicotine by all four assessors. Also, all four assessors evaluated the pouch product PPC1 to have a high burning (tingling) sensation.

Similarly, the pouch product PPC1 was evaluated with respect to perceived effect from nicotine in the same way as described above. The pouch product PPC1 was evaluated to have a high perceived effect from nicotine by all four assessors.

Example 7—User Evaluations

Pouches having a varying content of sugar alcohol and varying fiber identity were prepared in accordance with example 3G.

PPC101, PPC102 and PPC103 are pouches comprising nicotine, varying amounts of erythritol and either MCC or wheat fiber.

COMP.P1 and COMP.P2 are pouches comprising nicotine, no sugar alcohol and either MCC or wheat fiber.

The pouches were evaluated by a test-panel of 4 trained assessors. Each assessor evaluates all samples twice. The test-panel evaluated the pouches on 3 different parameters over 10 min: salivation effect, sweetness intensity and overall taste.

TABLE 12

| | | Minutes | | | | | | | | | |
|---|---|---|---|---|---|---|---|---|---|---|---|
| | | 1 | 2 | 3 | 4 | 5 | 6 | 7 | 8 | 9 | 10 |
| Salivation effect | COMP.P2 | 2 | 2 | 2 | 2 | 2 | 2 | 2 | 2 | 2 | 2 |
| | PPC102 | 2 | 2 | 2 | 2 | 2 | 2 | 2 | 2 | 2 | 2 |
| | PPC103 | 3 | 3 | 3 | 3 | 3 | 2 | 2 | 2 | 2 | 2 |
| | COMP.P1 | 2 | 2 | 2 | 2 | 2 | 2 | 2 | 2 | 2 | 2 |
| | PPC101 | 3 | 3 | 3 | 2 | 2 | 2 | 2 | 2 | 2 | 2 |
| Sweetness | COMP.P2 | 1 | 1 | 1 | 1 | 1 | 1 | 1 | 1 | 1 | 1 |
| | PPC102 | 2 | 2 | 2 | 2 | 2 | 2 | 2 | 2 | 2 | 2 |
| | PPC103 | 3 | 3 | 3 | 3 | 3 | 3 | 3 | 3 | 3 | 3 |
| | COMP.P1 | 1 | 1 | 1 | 1 | 1 | 1 | 1 | 1 | 1 | 1 |
| | PPC101 | 3 | 3 | 3 | 2 | 2 | 2 | 2 | 2 | 2 | 2 |
| Overall taste | COMP.P2 | 1 | 1 | 1 | 1 | 1 | 1 | 1 | 1 | 1 | 1 |
| | PPC102 | 3 | 3 | 3 | 2 | 2 | 2 | 2 | 2 | 2 | 2 |
| | PPC103 | 4 | 4 | 4 | 4 | 4 | 3 | 3 | 3 | 3 | 3 |
| | COMP.P1 | 2 | 2 | 2 | 2 | 1 | 1 | 1 | 1 | 1 | 1 |
| | PPC101 | 4 | 4 | 4 | 3 | 3 | 3 | 3 | 2 | 2 | 2 |

Ratings:
1: Low
2: Below medium
3: Medium
4: Above medium
5: High

The test panel found that the pouches containing sugar alcohol had an increased sweetness sensation. Pouches containing no sugar alcohol, COMP.P1 and COMP.P2, scored the lowest on sweetness, whereas pouches comprising 10% sugar alcohol scored higher, and pouches comprising 20% sugar alcohol scored even higher on sweetness.

The salivation effect was also evaluated. The test panel found that a pouch comprising MCC and a content of 20% sugar alcohol improved the salivation effect (PPC103). For pouches comprising wheat fiber, this improved salivation could be observed already at a content of 10% sugar alcohol (PPC101). This could further support that the water binding capacity of wheat fiber is higher than for MCC, thereby facilitating an increased salivation.

In general pouches comprising wheat fiber (COMP.P1 and PPC101) had an improved overall taste intensity compared to pouches comprising MCC (COMP.P2 and PPC102). The test panel further noted that COMP.P2 had a very salty taste, and that no lemon flavor could be perceived.

Furthermore, the test panel evaluated the mouthfeel of the pouches. COMP.P2 and PPC102 were found to have markedly less pleasant mouthfeel than PPC103, COMP.P1 and PPC101. For COMP.P2 and PPC102, the test panel noted that the pouch compositions were lumpy, the filling of the pouch was too low and that irritation of the gums were observed during use. None of this was observed for PPC103, COMP.P1 and PPC101.

For COMP.P1 and PPC101 the test panel noted that the pouches has a pleasant degree of filling, and the powder was moldable.

The use of fiber with increased water binding capacity could provide pouches with a more pleasant mouthfeel during use.

The invention claimed is:

1. An oral pouched product comprising
a saliva permeable pouch, and
a non-tobacco pouch composition,
the pouch composition comprising
heat-treated fibers,
nicotine in an amount of 0.1-5.0% by weight of the pouch composition,
water in an amount of 20-65% by weight of the pouch composition,
at least one sugar alcohol in an amount of 10-60% by weight of the pouch composition, wherein the at least one sugar alcohol is selected from xylitol, maltitol, mannitol, erythritol, isomalt, sorbitol, lactitol, and mixtures thereof, and
preservative selected from sorbic acid and its salts, benzoic acid and its salts, sulfur dioxide salts, nitrate salts, nitrite salts, acetic acid and its salts, lactic acid and its salts, malic acid and its salts in an amount of between 0.05% to 0.5% by weight of the pouch composition.

2. The oral pouched product according to claim 1, wherein the pouch composition further comprises a preservative in an amount of less than 0.3% by weight of the composition.

3. The oral pouched product according to claim 1, where the pouch composition comprises said heat-treated fibers in an amount of 5-50% by weight of the pouch composition.

4. The oral pouched product according to claim 1, wherein said heat-treated fiber is a plant fiber selected from wheat fibers, pea fibers, rice fiber, maize fibers, oat fibers, tomato fibers, barley fibers, rye fibers, sugar beet fibers, buckwheat fibers, potato fibers, cellulose fibers, apple fibers, bran fiber, bamboo fibers, powdered cellulose, cocoa fibers, cellulose fibers, and combinations thereof.

5. The oral pouched product according to claim 1, wherein the pouch composition further comprises a pH-regulating agent.

6. The oral pouched product according to claim 1, wherein the pouch composition comprises a pH-regulating agent in an amount of less than 6% by weight of the pouch composition.

7. The oral pouched product according to claim 6, wherein the pH-regulating agent is a basic pH-regulating agent selected from Sodium carbonate, Sodium bicarbonate, Potassium carbonate, Potassium bicarbonate, Magnesium carbonate, or any combination thereof.

8. The oral pouched product according to claim 1, wherein the at least one sugar alcohol comprises xylitol and/or erythritol.

9. The oral pouched product according to claim 1, wherein said at least one sugar alcohol comprises at least two sugar alcohols.

10. The oral pouched product according to claim 1, wherein the nicotine is selected from the group consisting of nicotine salts, nicotine free base, nicotine bound to an ion exchanger nicotine inclusion complexes or nicotine in any non-covalent binding, nicotine bound to zeolites, nicotine bound to cellulose, and mixtures thereof.

11. The oral pouched product according to claim 1, wherein the nicotine comprises nicotine mixed with ion exchange resin.

12. The oral pouched product according to claim 1, wherein the nicotine comprises a nicotine salt.

13. The oral pouched product according to claim 1, wherein the nicotine comprises nicotine bound to an ion exchange resin.

14. The oral pouched product according to claim 1, wherein the pouch composition further comprises a humectant.

15. The oral pouched product according to claim 1, wherein the pouch composition comprises a humectant in an amount of 0.5 to 10% by weight of the pouch composition.

16. The oral pouched product according to claim 1, wherein the pouch composition comprises a glidant in an amount of between 0.5 and 5% by weight of the pouch composition.

17. The oral pouched product according to claim 1, wherein the pouch composition comprises a flavor in an amount of 0.01 to 15% by weight of the pouch composition.

18. The oral pouched product according to claim 1, wherein the pouch composition comprises a preservative in an amount of 0.10 to 0.5% by weight of the pouch composition.

19. The oral pouched product according to claim 1, wherein the heat-treated fibers are water-insoluble, wherein water-insoluble refers to a water-solubility of less than 0.1 gram of composition or substance per 100 mL of water measured at 25 degrees Celsius and pH of 7.0.

20. The oral pouched product according to claim 1, wherein the pouch composition comprises the water in an amount of 20-50% by weight of the pouch composition.

21. The oral pouched product according to claim 1, wherein the pouch composition comprises the water in an amount of 20-40% by weight of the pouch composition.

22. The oral pouched product according to claim 1, wherein the pouch composition comprises the nicotine in an amount of 0.5 to 3.0% by weight of the pouch composition.

23. An oral pouched product comprising
a saliva permeable pouch, and
a non-tobacco pouch composition,
the pouch composition comprising
    heat-treated fibers,
    nicotine in an amount of 0.1-5.0% by weight of the pouch composition,
    water in an amount of 20-65% by weight of the pouch composition,
    at least one sugar alcohol in an amount of 10-60% by weight of the pouch composition, wherein the at least one sugar alcohol is selected from xylitol, maltitol, mannitol, erythritol, isomalt, sorbitol, lactitol, and mixtures thereof,
    preservative in an amount of between 0.05% to 0.5% by weight of the pouch composition,
wherein the pouch composition is substantially free of triglycerides.

24. An oral pouched product comprising
a saliva permeable pouch, and
a non-tobacco pouch composition,
the pouch composition comprising
    heat-treated fibers,
    nicotine in an amount of 0.1-5.0% by weight of the pouch composition,
    water in an amount of 20-65% by weight of the pouch composition,
    at least one sugar alcohol in an amount of 10-60% by weight of the pouch composition, wherein the at least one sugar alcohol is selected from xylitol, maltitol, mannitol, erythritol, isomalt, sorbitol, lactitol, and mixtures thereof,
    preservative in an amount of between 0.05% to 0.5% by weight of the pouch composition,
wherein the pouch composition has a total aerobic microbial count of no more than $5 \times 10^3$ CFU/gram.

* * * * *